United States Patent [19]

Yoshihama et al.

[11] Patent Number: 5,349,121
[45] Date of Patent: Sep. 20, 1994

[54] BIOLOGICALLY PURE MUSHROOM CULTURE AND METHOD FOR MUSHROOM CULTIVATION

[75] Inventors: Yoshio Yoshihama, Muko; Katsuhiko Kusakabe, Otsu; Susumu Matsui, Otsu; Hideo Morita, Otsu, all of Japan

[73] Assignee: Takara Shuzo Co., Ltd., Kyoto, Japan

[21] Appl. No.: 89,593

[22] Filed: Jul. 12, 1993

Related U.S. Application Data

[63] Continuation of Ser. No. 769,640, Oct. 1, 1990, abandoned.

[30] Foreign Application Priority Data

Mar. 7, 1991 [JP] Japan .................................. 3-065261

[51] Int. Cl.⁵ .......................... A01H 15/00; A01G 1/04
[52] U.S. Cl. ............................... 800/200; 800/DIG. 8; 47/1.1

[58] Field of Search ................. 47/1.1, 1.102; 800/DIG. 8, 200

[56] References Cited

U.S. PATENT DOCUMENTS

4,940,837  7/1990  Kawano et al. ..................... 800/200

FOREIGN PATENT DOCUMENTS

59-205977  11/1984  Japan .......................... C12N 1/14

OTHER PUBLICATIONS

Hongo, Trans. Mycol. Soc. Japan, 12:89-91 (1971).

Primary Examiner—David T. Fox
Assistant Examiner—Elizabeth F. McElwain
Attorney, Agent, or Firm—Wenderoth, Lind & Ponack

[57] ABSTRACT

A biologically pure culture of *Lyophyllum decastes* capable of forming a fruiting body in an artificial medium. Also provided is a method for cultivation of *Lyophyllum decastes* to form the fruiting body.

2 Claims, No Drawings

BIOLOGICALLY PURE MUSHROOM CULTURE AND METHOD FOR MUSHROOM CULTIVATION

This application is a continuation of now abandoned application, Ser. No. 07/769,640, filed Oct. 1, 1991.

This invention relates to a biologically pure culture and a method for the artificial cultivation of *Lyophyllum decastes*, a species of edible mushroom.

*Lyophyllum decastes* grows widely in locations close to human habitations, in fields, in woods, and elsewhere throughout the summer and autumn. It is strongly resembles *Lyophyllum shimeji* in shape The flavor is exceptionally good, and the meat of the fruiting body is somewhat more firm than that of *Lyophyllum shimeji*, giving an excellent texture when chewed; this mushroom is much prized for eating.

In recent years, such mushrooms species as *Flammulina velutipes*, *Pleurotus ostreatus*, *Lyophyllum ulmarium*, and *Pholiota nameko* have come to be artificially cultured on a culture medium with the main ingredients of sawdust and rice bran. Now it is possible to harvest these mushrooms throughout the year, with a reliable yield, without regard for season.

*Lyophyllum decastes*, like those species just listed, is an edible mushroom, so a number of culture methods have been investigated to find ones suitable for this species.

*Lyophyllum decastes* is saprophytic, which means that it would be difficult to grow it by bed-log cultivation as is done for *Lentinus edodes*, etc. Experiments have been done at the Fukushima Prefectural Forest Experiment Station, Japan, in which a medium with the main ingredient of composted bark and with added rice bran and wheat bran as nutrient sources was used in indoors bag cultivation, and then, bag cultivation in the field, in which the medium was buried in the earth was tried. The proportions of composted bark and rice bran used, by weight, were 10:1.5, and the water content at the time of medium preparation was 65%. One kilogram of medium was placed in each bag. The time development of fruiting bodies of *Lyophyllum decastes* is long, and fruiting bodies do not appear at one time; the time needed from inoculation to harvest, when harvest is taken to be at the time when the largest proportion of fruiting bodies appear, is different depending on the strain tested, with a range of about 180–240 days. In addition, the yield of fruiting bodies obtained by such culture is decreased because of contamination and the like, and the efficiency of this method of cultivation is low (Bull. Fukushima Pref. For. Expt. Stn. No. 19, 1986).

Another report on a method for cultivation in the field with the culture medium buried outside later appeared (Annual Report of Fukushima Pref. For. Expt. Stn. No. 20, 1988).

Japanese Laid-Open Patent Application 63-169913 discloses a method for the culture of *Lyophyllum decastes* in which the medium is a mixture of the following ingredients, by weight: 100 parts of sawdust and 0.5 to 0.6 part of chicken manure, leaf mold, ash, and bran, and in which cultivation is in a bottle. That method was not the ordinary bottle cultivation method. After removal of exposed mycelia and filling to the top of the bottle with water, the bottle is placed upside down for one week of culture, and then turned right side up for culture to continue. Compared to ordinary methods for mushroom cultivation in a bottle, this method requires much labor.

The purpose of this invention is to provide a biologically pure culture an a method for the artificial cultivation of *Lyophyllum decastes* in which this edible mushroom can be cultured in a short period of time, with good quality and low cost, on an industrial scale.

To summarize this invention, this invention comprises a biologically pure culture of *Lyophyllum decastes* selected from the group consisting of *Lyophyllum decastes* K-3303 (FERM P)-11320; FERM BP-4347), *Lyophyllum decastes* K-3304 (FERM P-1132; FERM P-4348), and *Lyophyllum decastes* K-3305 (FERM P-11322; FERM BP-4349) and a method for mushroom cultivation that uses artificial medium characterized by said mushroom being selected from the group consisting of *Lyophyllum decastes* K-3303 (FERM P-11320; FERM BP-4347), *Lyophyllum decastes* K-3304 (FERM P-11322; FERM BP-4348), and *Lyophyllum decastes* K-3305 (FERM P-11322; FERM BP-4349).

In general, even though mushrooms collected in a different place are of the same species, the speed of growth of their mycelia and the ability of the organisms to form fruiting bodies can be very different. We collected a number of *Lyophyllum decastes* from different locations, obtained biologically pure cultures from fruiting bodies of the *Lyophyllum decastes* collected, and examined them. We found that some of the strains obtained as described above could produce fruiting bodies at a high yield by artificial cultivation, making this invention possible.

The ability of the strains of *Lyophyllum decastes* collected to produce fruiting bodies was examined as follows. The medium used was PGY liquid medium (components: 0.2% peptone, 2.0% glucose, 0.2% yeast extract, 0.05% $KH_2PO_4$, and 0.05% $MgSO_4.7H_2O$, at pH 6.0). Strains of *Lyophyllum decastes* were inoculated into 100 ml of this medium, and cultured at 25° C. for 10 days to obtain a liquid seed culture Then 50 g of leaf mold, 50 g of cryptomeria sawdust, 100 g of rice bran, and 350 g of water were mixed well. The mixture was packed into a polypropylene wide-mouthed bottle with a 850-ml capacity. After a hole with a diameter of 1 cm was made from the center of the mouth of the bottle almost to the bottom, the bottle was stoppered with a cap, and was sterilized at 120° C. for 60 minutes, which resulted in a solid culture medium. The bottle was inoculated with 20 ml of the liquid seed culture and cultured in the dark at 25° C. and a humidity of 55% until mycelia were seen above the bottle. Culture was continued for 30 days more, after which the exposed mycelia were scraped off the top of the culture medium, together with about 1 cm of the culture medium itself, after which the bottle was filled to its top with water. The water was poured off 3 hours later, and the culture was continued with the illumination of 20 lux, at 15° C. and a humidity of 90%, during which time primordia of fruiting bodies formed. When the primordia had formed, culture was continued at 500 lux, 15° C., and 90% humidity until mature fruiting bodies had formed. We recorded the weight of fruiting bodies obtained, total culture period, and the shape of the fruiting bodies for each strain of *Lyophyllum decastes* investigated. The results are shown in Table 1.

TABLE 1

| Strain | Place collected | Total culture period (days) | Yield (g) | Shape |
|---|---|---|---|---|
| K-954 | Nara | 166 | 80 | X |

TABLE 1-continued

| Strain | Place collected | Total culture period (days) | Yield (g) | Shape |
| --- | --- | --- | --- | --- |
| K-1323 | Fukushima | Unsuccessful | | |
| K-1428 | Hokkaido | Unsuccessful | | |
| K-1807 | Aomori | Unsuccessful | | |
| K-2979 | Shiga | 141 | 115 | ○ |
| K-2980 | Osaka | 123 | 94 | X |
| K-3099 | Gunma | Unsuccessful | | |
| K-3230 | Kyoto | 155 | 124 | X |
| K-3303 | Switzerland | 87 | 147 | ⊚ |
| K-3304 | Switzerland | 88 | 141 | ⊚ |
| K-3305 | Switzerland | 90 | 150 | ⊚ |
| K-3343 | West Germany | 120 | 30 | ○ |
| IFO 30161 | | 139 | 83 | X |
| IFO 30260 | | 98 | 110 | ○ |
| IFO 31167 | | Unsuccessful | | |

The word "unsuccessful" in Table 1 means that fruiting bodies did not form during a total culture period of 180 days, and the symbol "⊚" means that the shape of fruiting bodies was excellent; similarly, "○" means good, and "X" means poor.

Table 1 shows that of the strains of mushrooms tested, three strains, K-3303, K-3304, K-3305, had a short total culture period of about 90 days, a satisfactory yield of about 140 g or more, and fruiting bodies that had caps and stipes of the same color and shape as fruiting bodies collected in the field; these qualities were especially satisfactory among the strains tested.

When the strains listed in Table 1 were cultured by the method disclosed in Japanese Laid-Open Patent Application 63-169913, in which there are the steps of removal of exposed mycelia, filling to the top of the bottle with water and reversal of the bottle, the effects were to decrease yield, if anything.

The morphological characteristics of the fruiting bodies and spores of the strains designated with a K-number among *Lyophyllum decastes* shown in Table 1 are as follows.

Shape: The fruiting body usually grows densely caespitose. The cap is about 5 cm in diameter and broadly convex. The color is buffy brown, becoming paler when the fruiting body ages. The surface is powdery-tomentose, especially in the center. The margin is incurved. Tissue: The color is white. The odor is more or less farinaceous. Gills: slightly yellowish white and crowed. Stipe: about 5 cm long, about 1 cm thick, of uniform thickness or slightly enlarged below, pale gray, solid or with mycelia crowded, elastic. Spore: globose or subglobose, smooth, 5.5–7.5×5–7 μm.

From these characteristics and by reference to *Colored Illustrations of Mushrooms of Japan* by Rokuya Imazeki and Tsuguo Hongo (Hoikusha, Osaka, Japan), vol.1, 1987, these strains have been identifies as strains of *Lyophyllum decastes*.

Among these strains tested, K-3303 has been named *Lyophyllum decastes* K-3303 and has been deposited at the Fermentation Research Institute, Agency of Industrial Science and Technology, Japan, under the accession number of FERM P-11320. Similarly, K-3304 and K-3305 have been deposited as *Lyophyllum decastes* K-3304 (FERM P-11321) and *Lyophyllum decastes* K-3305 (FERM P-11322).

Next, various properties of *Lyophyllum decastes* K-3303, K-3304, and K-3305 will be described. *Lyophyllum decastes* K-3303

(1) Malt-extract agar culture (20° C.)

With 10 days of incubation, colonies were 28 mm in diameter. Their color was white; there were many aerial hyphae. At 15 days, colonies were 48 mm in diameter. At 20 days, colonies were 67 mm in diameter and were dense and white, with mycelia stretching out straight horizontally from the center. There were many aerial hyphae. The underside of the colonies was uniform, with no variations in color.

(2) Potato-glucose agar culture (20° C.)

with 10 days of incubation, colonies were 28 mm in diameter. Their color was white; there were many aerial hyphae. At 15 days, colonies were 49 mm in diameter. At 20 days, colonies were 64 mm in diameter, and were dense and white, rising like a mat. There were many aerial hyphae. The underside of the colonies was uniform, with no variations in color.

(3) Oatmeal agar culture (20° C.)

With 10 days of incubation, colonies were 34 mm in diameter, with a few aerial hyphae, and radiational growth. At 5 days, colonies were 58 mm in diameter. At 20 days, colonies were 80 mm in diameter, white, and radiating. Aerial hyphae were more numerous than at 10 days. The underside of the colonies was uniform, with no variations in color.

(4) Culture on potato-glucose agar containing 0.1% gallic acid (20° C.; for detection of phenol oxidase)

With 10 days of incubation, there was little growth; colonies were 9 mm in diameter and white, with many aerial hyphae; there was a brownish zone 35 mm in diameter. At 20 days colonies were 15 mm in diameter, and the brownish zone was 50 mm. Colonies were white and rose.

(5) Optimum temperature for growth of mycelia we used mycelia grown on an agar disk 6 mm in diameter to inoculate to PGY agar medium and incubated the cultures at one of several different temperatures. We measured the diameter of each colony after 14 days of incubation. From the results, we estimated the optimum temperature to be around 25° C. and found that this strain could almost not grow at 5° C. and never grew at 30° C.

(6) Optimum pH for growth of mycelia

We used mycelia grown on an agar disk 6 mm in diameter to inoculate PGY liquid medium that was adjusted to one of several different pHs (each medium, 40 ml) and incubated the cultures at 25° C. After 14 days of incubation, we measured the dry weight of the mycelia. From the results, we estimated the optimum pH to be around 6. This strain could grow at pH 4 to 9. *Lyophyllum decastes* K-3304

(1) Malt-extract agar culture (20° C.)

With 10 days of incubation, colonies were 25 mm in diameter. Their color was white; there were many aerial hyphae. At 15 days, colonies were 44 mm in diameter. At 20 days, colonies were 65 mm in diameter, and were dense and white, with mycelia stretching out straight horizontally from the center. There were many aerial hyphae. The underside of the colonies was uniform, with no variations in color.

(2) Potato-glucose agar culture (20° C.)

With 10 days of incubation, colonies were 32 mm in diameter. Their color was white; there were many aerial hyphae. At 15 days, colonies were 53 mm in diameter. At 20 days, colonies were 69 mm in diameter, and were dense and white, rising like a mat. There were many aerial hyphae. The underside of the colonies was uniform, with no variations in color.

(3) Oatmeal agar culture (20° C.)

With 10 days of incubation, colonies were 31 mm in diameter, with a few aerial hyphae, and radiational growth. AT 15 days, colonies were 55 mm in diameter. At 20 days, colonies were 76 mm in diameter, white, and radiating. Aerial hyphae were more numerous than at 10 days. The underside of the colonies was uniform, with no variations in color.

(4) Culture on potato-glucose agar containing 0.1% gallic acid (20° C.; for detection of phenol oxidase)

With 10 days of incubation, thee was little growth; colonies were 9 mm in diameter and white, with many aerial hyphae; there was a brownish zone 36 mm in diameter. At 20 days, colonies were 18 mm in diameter, and the brownish zone was 52 mm. Colonies were white and rose.

(5) Optimum temperature for growth of mycelia

We used mycelia grown on an agar disk 6 mm inm diameter to inoculate to PGY agar medium and incubated the cultures at one of several different temperatures. We measured the diameter of each colony after 14 days of incubation. From the results, we estimated the optimum temperature to be around 25° C. and found that this strain could almost not grow at 5° C. and never grew at 30° C.

(6) Optimum pH for growth of mycelia

We used mycelia grown on an agar disk 6 mm in diameter to inoculate PGY liquid medium that was adjusted to one of several different pHs (each medium, 40 ml) and incubated the cultures at 25° C. After 14 days of incubation, we measured the dry weight of the mycelia. From the results, we estimated the optimum pH to be around 5. This strain could grow at pH 4 to 9. *Lyophyllum decastes* K-3305

(1) Malt-extract agar culture (210° C.)

With 10 days of incubation, colonies were 20 mm in diameter. Their color was white; there were many aerial hyphae. At 15 days, colonies were 325 mm in diameter. At 20 days, colonies were 49 mm in diameter, and were dense and white, with mycelia stretching out straight horizontally from the center. There were many aerial hyphae. There were radiating folds in the center of the underside, with no variations in color.

(2) Potato-glucose agar culture (20° C.)

with 10 days of incubation, colonies were 27 mm in diameter. Their color was white; there were many aerial hyphae. At 15 days, colonies were 42 mm in diameter. At 20 days, colonies were 57 mm in diameter, and were dense and white, rising like a mat. There were many aerial hyphae. There were radiating folds in the center of the underside, with no variations in color.

(3) Oatmeal agar culture (20° C.)

With 10 days of incubation, colonies were 33 mm in diameter, with a few aerial hyphae, and radiational growth. At 15 days, colonies were 53 mm in diameter. At 20 days, colonies were 73 mm in diameter, white, and radiating. Aerial hyphae were more numerous than at 10 days. There were radiating folds in the center of the underside, with no variations in color (4) culture on potato-glucose agar containing 0.1% gallic acid (20° C.; for detection of phenol oxidase)

With 10 days of incubation, there was little growth; colonies were 11 mm in diameter and white, with many aerial hyphae; there was a brownish zone 30 mm in diameter. At 20 days, colonies were 14 mm in diameter, and the brownish zone was 43 mm. Colonies were white and rose.

(3) Optimum temperature for growth of mycelia

We used mycelia grown on an agar disk 6 mm in diameter to inoculate to PGY agar medium and incubated the cultures at one of several different temperatures. We measured the diameter of each colony after 14 days of incubation. From the results, we estimated the optimum temperature to be around 25° C. and found that this strain could almost not grown at 5° C. and never grew at 30° C.

(6) Optimum pH for growth of mycelia

We used mycelia grown on an agar disk 6 mm in diameter to inoculate PGY liquid medium that was adjusted to one of several different pHs (each medium, 40 ml) and incubated the cultures at 25° C. After 14 days of incubation, we measured the dry weight of the mycelia. From the results, we estimated the optimum pH to be around 5. This strain could grow at pH 4 to 9.

Next, to learn how to distinguish *Lyophyllum decastes* K-3303, K-3304, and K-3305 from other strains of *Lyophyllum decastes*, we tried dual culture of PGY agar medium. The strains of *Lyophyllum decastes* examined were the 15 strains shown in Table 1. Dikaryons of each strain were excised from a stock culture (PGY agar slant medium) as a block (3×3×3 mm) and one block was placed next to a dikaryon block (3×3×3 mm) of *Lyophyllum decastes* K-3303, K-3304, and K-3305, with edges 1 cm apart, on PGY agar medium. After culture at 25° C. for 20 days, we judged whether an inhibition line had formed at the interface between the colonies or not. The results are shown in Table 2.

TABLE 2

|  | K-3303 | K-3304 | K-3305 |
|---|---|---|---|
| K-954 | + | + | + |
| K-1323 | + | + | + |
| K-1428 | + | + | + |
| K-1807 | + | + | + |
| K-2979 | + | + | + |
| K-2980 | + | + | + |
| K-3099 | + | + | + |
| K-3230 | + | + | + |
| K-3303 | − | + | + |
| K-3304 | + | − | + |
| K-3305 | + | + | − |
| K-3343 | + | + | + |
| IFO 30161 | + | + | + |
| IFO 30260 | + | + | + |
| IFO 31167 | + | + | + |

As shown in Table 2, the 13 strains tested all formed an inhibition line during dual culture with *Lyophyllum decastes* K-3303, K-3304 and K-3305. Thus, these three strains are new strains.

The strains of *Lyophyllum decastes* of this invention can be cultured by ordinary methods of artificial cultivation.

To explain the method in more detail, the usual method for artificial cultivation is the method used for the culture of *Flammulina velutipes, Pleurotus ostreatus, Lyophyllum ulmarium*, and such mushrooms. There are methods of bottle culture, bag culture, box culture, etc., but here, the method of bottle culture will be used as an example. This method involves the preparation of medium, the filling of the bottles with medium, their serialization, their inoculation, their culture, the removal of exposed mycelia, sprouting, growth, and harvesting. The preparation of medium involves the mixture of the usual ingredients used in artificial culture, which are sawdust, rice bran, wheat bran, barley powder, etc., with water added to give a moist medium; it is desirable to add leaf mold, composted bark, composted wheat, composted waste culture medium, compost, and no on, and the water content should be 60-75%, and more preferably about 65%. The composition of the medium should be any composition suitable for the ready formation of fruiting bodies of *Lyophyllum decastes*; one example is a mixture of sawdust, leaf mold, and rice bran as a source of nutrients. The leaf mold contains growth factors and the like needed for saprophytic growth. The proportion by weight of leaf mold added to the medium should be 1% or more, and preferably 5% or more. The bottle used for culture should have the capacity of 800-1000 ml, and preferably, 850 ml; it should be a wide-mouthed culture vessel made of polypropylene. The amount of medium put into the bottle should be 450-750 g, and more preferably, 550 g, and a hole with a diameter of about 1 cm should be opened from the center of the mouth of the bottle almost to the bottom, after which the bottle is stoppered with a cap, which is called the step of filling the bottle with medium. For the sterilization, all of the microorganisms in the medium are killed with steam, which is done at ordinary pressure at 98° C. for 4 to 5 hours, or at high pressure at 120° C. for 30 to 90 minutes. Inoculation is done after the cooling of the medium by the addition of a portion of seed culture, prepared by the culture of *Lyophyllum decastes* at 25° C. for 10 to 15 days in PGY liquid medium. Some 20 ml of seed culture should be transferred to each bottle without allowing contamination of the culture. The culture medium obtained by the steps described up to here can be cultured for 30 to 40 days at 25° c., in which time the mycelia of *Lyophyllum decastes* have extended throughout the culture medium, which culture medium can be used as solid seed culture. Then some 15 g of the solid seed culture should be transferred to each bottle without allowing contamination. Culture is at the temperature of 20° to 25° C. after the inoculation of the culture medium, at a humidity of 40-70%, until the mycelia have extended themselves throughout the medium, and in the next step of growth, culture is continued for 40 to 120 days, and preferably for about 80 days. For removal of exposed mycelia, the area where the seed culture was used for inoculation and the surface of the cultured medium are scraped, which induces the formation of primordia, and after removal of the exposed mycelia in this way, the bottle is filled to its top with water, and the water is poured off in 3 to 5 hours. Sprouting is the step in which the primordia of the fruiting body form, and this occurs during culture at 10° to 20° C., and preferably during culture at 15° C.; at a humidity of 80% or more, an preferably at a humidity of 85 to 95%; with illumination of 500 lux or less, and preferably with illumination of 50 lux or less; for 10 to 20 days. The step of growth involves the formation of mature fruiting bodies from thee primordia, which occurs during culture at 10° to 20° C., and preferably during culture at about 15° C.; at a humidity of 80% or more, and preferably at a humidity of 85 to 95%; with illumination of 50 lux or more, and preferably with illumination of 200 to 500 lux; for 5 to 15 days. The step of harvesting is the final step of cultivation. The example given above in the explanation is of bottle culture, but this invention is not limited to bottle culture alone.

EXAMPLE 1.

*Lyophyllum decastes* K-3303 (FERM P-11320) was used to inoculate 100 ml of PGY liquid medium (components: 0.2% peptone, 2.0% glucose, 0.2% yeast extract, 0.05% $KH_2PO_4$, and 0.05% $MgSO_4$, $7H_2O$, at pH 6.0), this was cultured for 10 days at 25° C. to give a liquid seed culture. In a wide-mouthed bottle made of polypropylene and with the capacity of 850 ml, the following were added after being thoroughly mixed: 50 g of leaf mold (Kotohira Co.), 50 g of cryptomeria sawdust, 100 g of rice bran, and 350 ml of water. The mixture was packed firmly into the bottle, and a hole with a diameter of 1 cm was opened from the center of the mouth of the bottle almost to the bottom, and the bottle was stoppered with a cap. Then the bottle was sterilized at 120° C. for 60 minutes and was cooled, which resulted in a solid culture medium. This medium was inoculated with 20 ml of the liquid seed culture described above, and cultured in the dark at 25° C. and a humidity of 55% until mycelia appeared above the culture medium, which took 35 days of culture. Culture was continued for 30 days more, after which the exposed mycelia were scraped off the top of the culture medium, together with about 1 cm of the culture medium itself, after which the bottle was filled to its top with water. The water was poured of 3 hours later, and culture was continued with the illumination of 20 lux at 15° C. and a humidity of 90% for 10 days, during which time primodia of fruiting bodies formed. Then the culture medium with the formed fruiting bodies was kept under illumination of 500 lux at 15° C. and a humidity of 90% for 12 days of continued culture, during which time mature fruiting bodies formed. The fruiting bodies of *Lyophyllum decastes* K-3303 (FERM P-11320) that were harvested had an excellent shape that closely resembled the shape of *Lyophyllum decastes* found in nature, and the flavor was excellent. The yield of fruiting bodies from each bottle was a mean of 147 g, and the total time of culture was 87 days.

EXAMPLE 2.

*Lyophyllum decastes* K-3304 (FERM P-11321) was used to inoculate 100 ml of PGY liquid medium, this was cultured for 10 days at 25° C. to give a liquid seed culture. In a wide-mouthed bottle made of polypropylene and with the capacity of 850 ml, the following were added after being thoroughly mixed: 50 g of composted bark (Fujimikogyo Co.), 50 g of cryptomeia sawdust, 100 g of rice bran, and 350 ml of water. The mixture was packed firmly into the bottle, and a hole with a diameter of 1 cm was opened from the center of the mouth of the bottle almost to the bottom, and the bottle was stoppered with a cap Then the bottle was sterilized at 120° C. for 60 minutes and was cooled, which resulted in a solid culture medium. This medium was inoculated with 20 ml of the liquid seed culture described above, and cultured in the dark at 25° C. and a humidity of 55% until mycelia appeared above the culture medium, which took 35 days of culture. Culture was continued for 30 days more, after which the exposed mycelia were scraped off the top of the culture medium, together with about 1 cm of the culture medium itself, after which the bottle was filled to its top with water. The water was poured off 3 hours later, and culture was continued with the illumination of 20 lux at 15° C. and a humidity of 90% for 11 days, during which time primodia of fruiting bodies formed. Then the culture medium with the formed fruiting bodies was kept under illumination of 500 lux at 15° C. and a humidity of 90% for 12 days of continued culture, during which time mature fruiting bodies formed. The fruiting bodies of *Lyophyllum decastes* K-3304 (FERM P-11321) that were harvested had an excellent shape that closely resembled the shape of

*Lyophyllum decastes* found in nature, and the flavor was excellent. The yield of fruiting bodies from each bottle was a mean of 135 g, and the total time of culture was 88 days.

EXAMPLE 3.

*Lyophyllum decastes* K-3305 (FERM P-11322) was used to inoculate 100 ml of PGY liquid medium, this was cultured for 10 days at 25° C. to give a liquid seed culture In a wide-mouthed bottle made of polypropylene and with the capacity of 850 ml, the following were added after being thoroughly mixed: 50 g of leaf mold (Kotohira Co.), 50 g of beech sawdust, 100 g of rice bran, and 350 ml of water. The mixture was packed firmly into the bottle, and a hole with a diameter of 1 cm was opened from the center of the mouth of the bottle almost to the bottom, and the bottle was stoppered with a cap. Then the bottle was sterilized at 120° C. for 60 minutes and was cooled, which resulted in a solid culture medium. This medium was inoculated with 20 ml of the liquid seed culture described above, and cultured in the dark at 25° C. and a humidity of 55% until mycelia appeared above the culture medium, which took 35 days of culture. Culture was continued for 30 days more, after which the exposed mycelia were scraped off the top of the culture medium, together with about 1 cm of the culture medium itself, after which the bottle was filled to its top with water. The water was poured off 3 hours later, and culture was continued with the illumination of 20 lux at 15° C. and a humidity of 90% for 12 days, during which time primodia of fruiting bodies formed. Then the culture medium with the formed fruiting bodies was kept under illumination of 500 lux at 15° C. and a humidity of 90% for 13 days of continued culture, during which time mature fruiting bodies formed. The fruiting bodies of *Lyophyllum decastes* K-3305 (FERM P-11322) that were harvested had an excellent shape that closely resembled the shape of *Lyophyllum decastes* found in nature, and the flavor was excellent. The yield of fruiting bodies from each bottle was a mean of 150 g, and the total time of culture was 90 days.

EXAMPLE 4.

In a wide-mouthed bottle made of polypropylene and with the capacity of 850 ml, the following were added after being thoroughly mixed: 50 g of leaf mold (Kotohira co.), 50 g of cryptomeria sawdust, 100 g of rice bran, and 350 ml of water. The mixture was packed firmly into the bottle, and a hole with a diameter of 1 cm was opened from the center of the mouth of the bottle almost to the bottom, and the bottle was stoppered with a cap. Then the bottle was sterilized at 120° C. for 60 minutes and was cooled, which resulted in a solid culture medium. This medium was inoculated with the liquid seed culture of *Lyophyllum decastes* K-3303 (FERM P-11320) which prepared as described in example 1 and cultured for 30 days at 25° C. and a humidity of 55%, which resulted in the solid seed culture. A solid culture medium wa prepared as described in Example 1 using 50 g of composted bark (Fujimikogyo Co.), 50 g of cryptomeria sawdust 100 g of rice bran, and 350 ml of water. This medium was inoculated with the solid seed culture without allowing contamination of the culture and cultured as described in Example 1. The fruiting bodies of *Lyophyllum decastes* K-3303 (FERM P-11320) that were harvested had an excellent shape, and the flavor was excellent. The yield of fruiting bodies from each bottle was a mean of 145 g, and the total time of culture was 87 days.

As described in detail above, by the biologically pure culture of *Lyophyllum decastes* and the culture method of this invention, it is possible to culture *Lyophyllum decastes* that have an excellent shape and flavor in high yield in a short period of time.

What we claim is:

1. A biologically pure culture of a strain belonging to *Lyophyllum decastes* capable of forming a fruiting body of about 140 grams or more per 550 grams of artificial medium containing sawdust, rice bran, and leaf mold or composted bark, for about 90 days cultivation and having all the identifying characteristics of *Lyophyllum decastes*, selected from the group consisting of *Lyophyllum decastes* K-3303 (FERM P-11320; FERM BP 4347), *Lyophyllum decastes* K-3304 (FERM P-11321; FERM BP4348), and *Lyophyllum decastes* K-3305 (FERM P-11322; FERM BP4349).

2. A method for cultivation of *Lyophyllum decastes* to form a fruiting body, which comprises a step of inoculating a strain of claim 1 to an artificial medium containing sawdust and rice bran, and a cultivating step of cultivating said strain under conditions effective to form said fruiting body, which cultivation step does not include cultivating said strain while said medium is upside down.

* * * * *